United States Patent [19]

Ballé et al.

[11] Patent Number: 4,704,447

[45] Date of Patent: Nov. 3, 1987

[54] POLYHYDROXY COMPOUNDS CONTAINING UREA GROUPS AND EITHER ESTER OR AMIDE GROUPS, PROCESS FOR THEIR PREPARATION, AND THE USE THEREOF

[75] Inventors: Gerhard Ballé; Gerhard Grögler, both of Leverkusen; Walter Meckel, Neuss, all of Fed. Rep. of Germany

[73] Assignee: Bayer Aktiengesellschaft, Leverkusen, Fed. Rep. of Germany

[21] Appl. No.: 824,042

[22] Filed: Jan. 30, 1986

[30] Foreign Application Priority Data

Feb. 13, 1985 [DE] Fed. Rep. of Germany ....... 3504967

[51] Int. Cl.$^4$ .................. C08G 18/34; C08G 18/32; C08G 18/00
[52] U.S. Cl. ........................ 528/84; 528/85; 528/78; 521/164
[58] Field of Search .................. 528/84, 85, 78; 521/164

[56] References Cited

U.S. PATENT DOCUMENTS

| | | | |
|---|---|---|---|
| 3,017,391 | 1/1962 | Mottus et al. | 260/78 |
| 4,448,905 | 5/1984 | Lin et al. | 521/164 |
| 4,454,259 | 6/1984 | Reischl et al. | 523/129 |
| 4,521,545 | 6/1985 | Kerimis et al. | 521/107 |
| 4,587,275 | 5/1986 | Kopp et al. | 521/163 |

OTHER PUBLICATIONS

H. K. Reinschuessel, "Lactams", Kinetics and Mechanisms of Polymerisations, vol. 2, pp. 303-326.

Primary Examiner—John Kight
Assistant Examiner—Dennis R. Daley
Attorney, Agent, or Firm—Gene Harsh; Joseph C. Gil; Lyndanne M. Whalen

[57] ABSTRACT

The compounds of the present invention are obtained by the reaction of carbamoyl lactams (from lactams and polyisocyanates) with polyhydric alcohols or monoamino alcohols in the presence of catalytic quantities of a strong basic catalyst, e.g. an alkali metal alcoholate, at elevated temperatures.

The polyols contain urea groups and either ester or amide groups and correspond to formula (I) or (II)

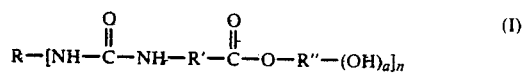

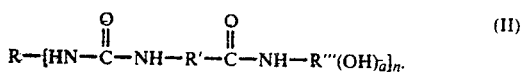

The polyols are crystalline, relatively high melting compounds which are used as reactants for the synthesis of polyurethane elastomers, in particular in the form of finely divided components in one-component polyurethane reaction mixtures.

12 Claims, No Drawings

POLYHYDROXY COMPOUNDS CONTAINING UREA GROUPS AND EITHER ESTER OR AMIDE GROUPS, PROCESS FOR THEIR PREPARATION, AND THE USE THEREOF

BACKGROUND OF THE INVENTION

The present invention relates to polyhydroxy compounds containing urea groups and either ester or amide groups, a process for their preparation, and their use.

Carbamoyl lactams, i.e. the adducts of lactams and isocyanates, are known compounds which are of technical interest in polyurethane and polyamide chemistry. The addition products of lactams (in particular of ε-caprolactam) with polyisocyanates or with isocyanate functional prepolymers of polyisocyanates and polyols, polyamines or polyaminopolyols, are known as masked isocyanates which are unreactive under conditions of storage. They may be formulated with isocyanate reactive compounds (such as polyols) for the preparation of one-component systems which do not harden until the lactam adduct is split up into its components by heating. The lactam can then be detected as volatile product of decomposition while the urethane group is in the product left behind, e.g.

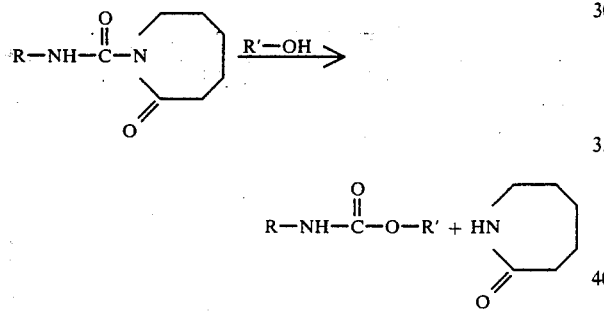

This principle of isocyanate masking is used mainly in the field of lacquers although the temperatures required to release decomposition of the addition product are generally very high (e.g. in the case of ε-caprolactam, above 160° C.).

Acyl lactams play a role in the chemistry of amino acids and peptides. It is known that acyl lactams open the lactam ring by hydrolysis. The reaction conditions must be very carefully chosen and controlled to ensure that ring opening is not accompanied or replaced by splitting off of the acyl group.

Acyl lactams and carbamoyl lactams play an important role in activated anionic lactam polymerization, where they function as the carriers of chain starting and chain growth. For information on the mechanism of anionic lactam polymerization, see U.S. Pat. No. 3,017,391; and H. K. Reinschuessel, "Lactams", in Kinetics and Mechanisms of Polymerizations, Vol. 2, Ring Opening Polymerizations, publishers K. C. Frisch, pages 303–326, M. Dekker, New York, 1969.

We have now found that the carbamoyl lactam ring can be opened by alcohols under relatively mild conditions if catalytic quantities of strong bases are present according to the following reaction scheme:

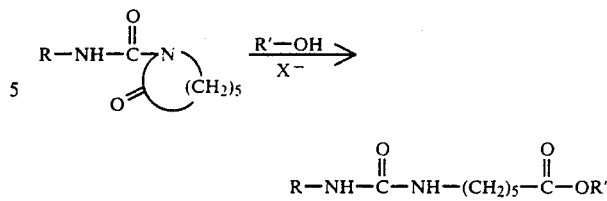

$X^-$ = base, e.g. alcoholate anion. This reaction proceeds smoothly and with high yields even under relatively mild conditions, e.g. in boiling methanol or ethanol. The side reaction of urethane formation with splitting off of lactam is not found to take place.

If a polyol is used as alcohol component, then new polyhydroxy compounds are obtained, which contain urea groups in addition to the hydroxy and ester group according to the following reaction scheme:

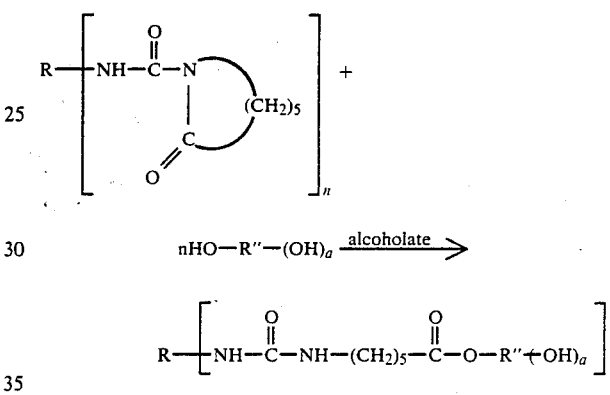

In the above formulae, R represents the hydrocarbon or heterocyclic group of a polyisocyanate having the functionality n and R'' represents the group of a polyhydric alcohol having the functionality (a+1).

If the alcohol is replaced by an amino alcohol, the reaction does not result in amino esters but in the corresponding hydroxyamides due to a concomitant or subsequent molecular rearrangement according to the following scheme:

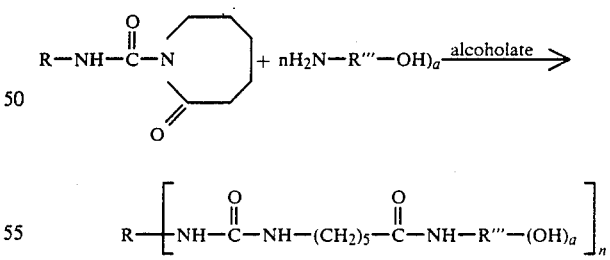

DESCRIPTION OF THE INVENTION

The present invention therefore relates to polyhydroxy compounds containing urea groups as well as ester or amide groups in accordance with the general formula (I) or (II)

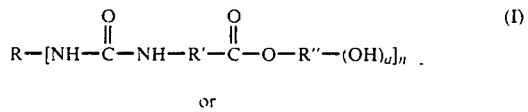

or

-continued

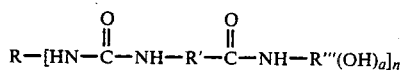

wherein
R represents the residue of an aliphatic, cycloaliphatic, aromatic or heterocyclic polyisocyanate which isocyanate may be a modified polyisocyanate or of an isocyanate prepolymer and in particular represents a $C_2$–$C_{36}$-alkylene, a $C_5$–$C_{15}$-cycloalkylene, a $C_6$–$C_{15}$-arylene or a heterocyclic group having the valency n;

R' represents a $C_3$–$C_{11}$-alkylene group, preferably a $C_3$, $C_4$, $C_5$, $C_{10}$ or $C_{11}$-alkylene group and most preferably a $C_5$-alkylene group;

R" represents the residue of a polyhydric alcohol having the functionality (a+1);

R''' represents the residue of a monoamino alcohol having the hydroxyl functionality a and a is an integer having a value $\geq 1$, is preferably 1 to 5, is more preferably 1 to 3 and is most preferably 1 or 2, and n represents 2 to 6, preferably 2 to 3.

Those polyhydroxy compounds of formulae (I) and (II) are preferred in which

R represents a group corresponding to one of the following formulae:

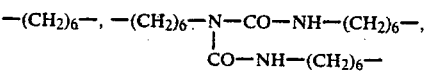

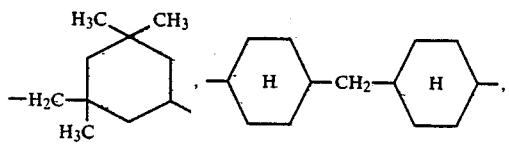

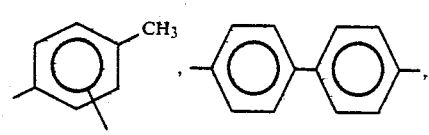

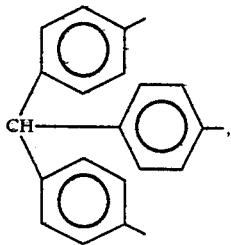

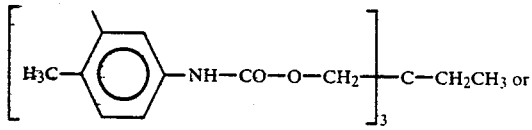

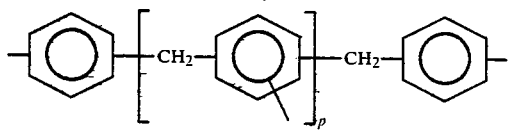

wherein p=0 to 5,

R' represents a group consisting to one of the following formulae: —$(CH_2)_3$—, —$(CH_2)_4$—, —$(CH_2)_5$— or —$(CH_2)_{11}$—, and most preferably a —$(CH_2)_5$— group;

R" represents a linear or branched aliphatic group or a cycloaliphatic group having (a+1) free valencies, and R''' represents a linear or branched aliphatic group or a cycloaliphatic group having (a+1) free valencies.

The invention further relates to a process for the preparation of polyhydroxy compounds (I) and (II), characterized in that compounds containing carbamoyl lactam groups in accordance with the general formula (III)

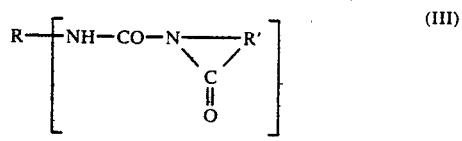

are reacted with a polyhydric alcohol of the formula (IV) or a monoamino alcohol of formula (V)

(IV)    (V)

wherein R, R', R" and R''' and n and a have the meanings indicated above, in the presence of catalytic quantities of a strongly basic catalyst (suitably an alkali metal base, e.g. an alkali metal alcoholate) at elevated temperatures of up to 200° C., and preferably from 80° to 160° C. The catalyst used is preferably an alkali metal alcoholate derived from the polyhydric alcohol or amino alcohol used. The starting material (III) preferably consists of addition products of lactams with aliphatic, cycloaliphatic, aromatic or heterocyclic polyisocyanates or modified isocyanates thereof or prepolymers containing isocyanate groups.

The new compounds are suitable for use as polyols in polyurethane chemistry, for example as crosslinking agents or chain-lengthening agents. It is of interest to be able to introduce urea groups into the macromolecule without having to use polyamines as crosslinking agents. Since the products all have a high melting point (from above 150° C. to above 200° C.), they are of particular interest as finely divided, heterogeneous chain-lengthening agents in storage-stable one-component systems.

A further object of the present invention is therefore the use of polyhydroxy compounds having the composition (I) or (II) as reactants for the synthesis of both homogeneous and cellular polyurethanes by the isocyanate polyaddition process. In particular, the polyhydroxyl compounds of the present invention are used as chain-lengthening agents or crosslinking agents for the synthesis of solid or cellular polyurethane elastomers based on low melting, relatively high molecular weight polyhydroxyl compounds, polyisocyanates and chain-lengthening agents used in quantities corresponding to approximately equivalent quantities of isocyanate groups to isocyanate reactive groups. Particularly interesting is their use in a finely divided, heterogeneous form in mixtures of low melting, relatively high molecular weight polyhydroxyl compounds and polyisocyanates or in the isocyanate prepolymers formed from the mixtures to form storage-stable one-component systems which are converted into polyurethane elastomers only when subsequently heated to about 100° to 200° C.

When a polyfunctional carbamoyl lactam of formula (III) is reacted with a polyalcohol $R''-(OH)_{a+1}$, (for example a glycol) polyaddition leading to relatively high molecular weight products is possible in principle. In order to obtain uniform 1:2 adducts, it is advisable to use a relatively large excess of the polyhydric alcohol, which then functions as reaction medium at the same time.

The alcoholate anion required may suitably be that of the polyhdyric alcohol or amino alcohol used in the process, and may be obtained by the addition of an alkali metal or of a strongly basic alkali metal compound (e.g. an alkali metal hydroxide) or of an alkali metal alcoholate. The alcohol introduced by way of the alcoholate is advantageously off from the equilibrium reaction mixture formed in order to avoid its reaction with the lactam. The reaction of the polyhydric alcohol with the carbamoyl lactam III is carried out by adding the latter to the solution of catalyst in the polyhydric alcohol, which is heated to about 80° to 150° C., in which it rapidly goes into solution. At the same time, the expected ureido alkane carboxylic acid ester polyol (e.g. the ureido carboxylic acid ester polyol) begins to separate from the product. The progress of the reaction can be followed by simple analytical methods, suitably by thin layer chromatography. When the starting material has been used up, the reaction mixture is neutralized with a suitable acid, e.g. an aqueous mineral acid, and the suspension is filtered, optionally after dilution with an organic solvent (such as methanol, ethanol or acetone) or with water (if the polyol alcohol used is miscible with water). Any salts and polyalcohol in the end product are removed by washing with water and solvent. The products are then sufficiently pure. The mother liquors and washing solutions may be separated by distillation and solvents as well as unreacted polyhydric alcohol may be returned to the process.

The polyfunctional carbamoyl lactams used as starting materials are obtained by the addition of lactams to polyisocyanates. The polyisocyanate components used may in principle be any polyisocyanate. Obviously preferred are commercially available polyisocyanates, e.g. tolylene diisocyanate in the form of pure, 2,4- and 2,6-isomers or of commercially produced isomeric mixtures; 4,4'-diisocyanatodiphenylmethane or its 2,4'- and 2,2'-position isomers and its isomeric mixtures and relatively high molecular weight multi-nuclear homologues; hexamethylene diisocyanate and its relatively high molecular weight modification products such as polyisocyanates containing biuret groups; isophorone diisocyanate; 4,4'-diisocyanatodicyclohexylmethane; the isomeric xylylene diisocyanates, α,α,α',α',-tetramethyl-m/p-xylylene diisocyanates; or 4,4',4''-triisocyanatotriphenylmethane. Prepolymers of polyisocyanates containing isocyanate groups are also suitable, e.g. an addition product of 1 mol of trimethylolpropane with 3 mol of tolylene diisocyanate or an addition product of 1 mol of dipropylene glycol with 2 mol of hexamethylene diisocyanate. Other suitable polyisocyanates are known and described in German Offenlegungsschriften Nos. 2,854,384 and 2,920,501.

Examples of suitable lactams include pyrrolidone-2, piperidone-2, ε-carpolactam and lauric lactam. The preferred lactam is ε-caprolactam.

The polyhydric alcohols IV and amino alcohols V should be liquid at the reaction temperature. Suitable polyol components are in particular glycols such as ethylene glycol and propylene glycol and their oligomers, e.g. di-, tri- and tetra-ethylene glycol and -propylene glycol, 1,3-propanediol; 1,2-, 1,3-, 1,4- and/or 2,3-butanediol; and 1,6-hexanediol.

The method of preparation of the urea amide polyols II is substantially similar but instead of using a glycol or higher functional polyhydric alcohol such as trimethylolpropane or glycerol or tetritols or hexitols, a monoamino alcohol or monoamino polyalcohol is used. Examples include ethanolamine, diethanolamine, propanolamine, dipropanolamine, and the like. It is found that the amino group will not to react with the carbamoyl lactam group under the reaction conditions, even in the presence of the alkaline catalyst. When using alkanolamines it is the hydroxyl group which reacts with the carbamoyl lactam, forming an ester with aminoalkyl end groups, which rearranges under the reaction conditions to the stable product of the formula II.

When reacting III (e.g. n=2) with a mono-alkanolamine about equivalent portions (e.g. 2 moles mono-alkanolamine per 1 mol III, n=2) may be reacted. When reacting III with polyols, it is preferred to use an excess of polyols over III (for example up to 5 OH-equivalents per lactam group) as to avoid the formation of some oligomers. Instead, the amino alcohol may be used in the calculated stoichiometric quantity (one amino group per lactam group).

The solvent or diluent used may be, for example, dioxane, but toluene is particularly suitable although it will not dissolve lower amino alcohols. The amino alcohol, for example, may be suspended in toluene. An alkali metal alcoholate or hydroxide is then added and the alcohols and water which are released in equilibrium are distilled off together with the toluene. Lactam adduct III is then added at the given reaction temperature. The product is obtained in a finely divided, easily filtered form.

The catalysts used may be, for example, sodium or potassium hydroxide, optionally in the form of alcoholic solutions, or the sodium or potassium alcoholates, e.g. Na or K-methanolate, ethanolate or tert.-butanolate. They are put into the process in quantities of 1 to 10%, preferably 1 to 5%, by weight, based on the carbamoyl lactam compound.

The OH functional compounds I and/or II according to the invention may be reacted with polyisocyanates in known manner, in particular in combination with relatively high molecular weight (molecular weight 400 to 6000), low melting (<60° C.) polyols, e.g. the usual polyether or polyester polyols. For this reaction, the solid polyols I or II are preferably used in a finely divided form with a particle size of preferably 1 to 100 μm, in particular 5 to 50 μm, if necessary after a grinding process. They are thus preferably present in a heterogeneous phase in the reaction mixture. The pot life (processing time) of such systems depends, of course, on the reactivity of the polyols or polyisocyanates present in the homogeneous phase. On the application of heat, however, the polyaddition of these components initially takes place virtually without any participation of the OH functional compounds of the invention which are present in the heterogeneous phase. It is thus possible to obtain prepolymers which are stable in storage at room temperature and which may subsequently be hardened whenever desired by a heat shock (120° to 200° C.) optionally under pressure and with shaping.

It is preferred, however, to employ a process known in the art in which a prepolymer containing isocyanate groups is reacted with the compounds according to the invention in the heterogeneous phase. This process, as is well known, results in end products with an orderly arrangement of hard and soft segments and improved mechanical properties. The mixtures of isocyanate prepolymers and the finely divided solid, high melting chain lengthening agents have a long pot life and storage life at room temperature, especially in the absence of additional catalysts. The advantage of such reaction mixture is, therefore, that the systems have a high stability in storage due to the high melting point and the low solubility of the chain lengthening agents according to the invention in the isocyanate prepolymer at room temperature. These long term reactive systems may be hardened at any subsequent time at elevated temperature, optionally after the addition of a hardening catalyst.

The invention is further illustrated, but is not intended to be limited by the following examples in which all parts and percentages are by weight unless otherwise specified.

EXAMPLES

Example 1

Preparation of hexane-1,6-bis-carbamoyl-ε-caprolactam as starting material

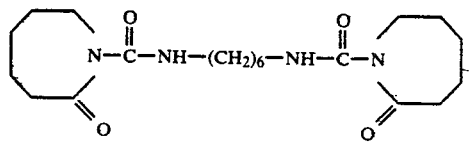

226 g (2 mol) of ε-caprolactam are melted at 80° C., briefly dehydrated under vacuum and reacted with 168 g (1 mol) of 1,6-hexanediisocyanate with occasional cooling. When the isocyanate groups have been completely used up (IR spectrum, titration) the melt is poured out onto a metal plate to solidify and is broken down into small pieces. The product can be recrystallized from toluene/cyclohexane mixtures.

Mp. 84° to 85° C.

N Calculated for $C_{20}H_{34}N_4O_4$ (394): 14.2%. Found: 14.0%.

Example 2

Hexane-1,6-bis-ureido-caproic acid-2-hydroxyethyl ester (according to the invention)

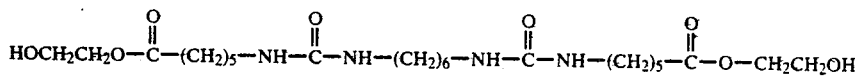

394 g of the bis-carbamoyl lactam from Example 1 are suspended in 1000 ml (about 18 mol) of ethylene glycol. After the addition of 10 g of sodium methylate solution (about 30% in methanol), the methanol is distilled off under vacuum at 80° C. and the mixture is then heated to 110° C. After disappearance of the starting material in the thin layer chromatogram (silica gel; chloroform/methanol 95:5, colored by iodine vapor) the dense, finely divided precipitate formed (the separation of which may be completed by dilution with ethanol) is suction filtered, washed with ethanol and dried. The product may be recrystallized from methanol or ethanol. The mother liquors and washing solutions may be separated by distillation to recover the unreacted glycol and the ethanol.

Mp. 155° to 157° C.

N Calculated for $C_{24}H_{46}N_4O_8$ (518): 10.8%. Found 10.9%.

IR spectrum: 1732 cm$^{-1}$ (ester), 1625 cm$^{-1}$ (aliphatic, substituted urea), 1580 cm$^{-1}$ (NH deformation).

Mass spectrum (DCI): Fragments with mass numbers 202 and 359 agree with the structure.

Example 3

Hexane-1,6-bis-ureido caproic acid-4-hydroxy butyl ester (according to the invention)

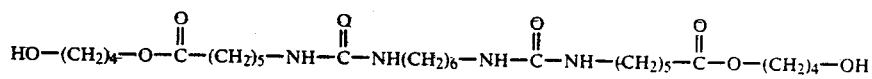

The reaction described in Example 2 was repeated with 1,4-butanediol as polyol component. The product, which was isolated by the same method, melts at 143° to 145° C.

N Calculated for $C_{28}N_{54}N_4O_8$ (574): 9.76%. Found: 9.8/9.8%.

IR spectrum: As in Example 2.

Mass spectrum (DCI): Fragments with mass numbers 73, 117, 230 and 344, in agreement with the above structure.

Example 4

Hexane-1,6-bis-ureido caproic acid-6-hydroxy hexyl ester (according to the invention)

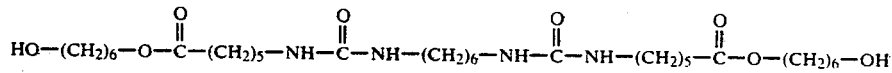

The method was the same as in Example 2 but using 1,6-hexanediol as the polyol.

Mp. 135° C.

N Calculated for $C_{32}H_{62}N_4O_8$ (630): 8.9%. Found: 8.9/9.1%.

IR and mass spectrum (DIC) in agreement with the structure.

Example 5

4,4'-diphenylmethane-bis-carbamoyl-2-caprolactam (starting material)

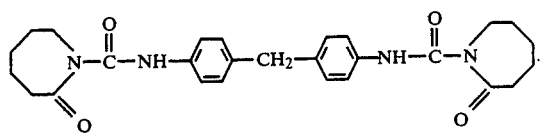

500 g of ε-caprolactam (4.4 mol) was dissolved in 400 ml of toluene, the solution was dehydrated by partial distillation, and a solution of 500 g of 4,4'-diisocyanatodiphenylmethane in 400 ml of toluene was then added dropwise at 80° C. in the course of one hour. When the reaction was completed (all the isocyanate groups used up) the precipitate formed was suction filtered and washed, first with toluene and then with petroleum ether, and dried.

Mp. 180°–182° C.

N Calculated for $C_{27}H_{32}N_4O_4$ (476): 11.76%. Found: 11.6/11.7%.

Example 6

4,4'-diphenylmethane-bis-ureido caproic acid-2-hydroxyalkyl ester (according to the invention)

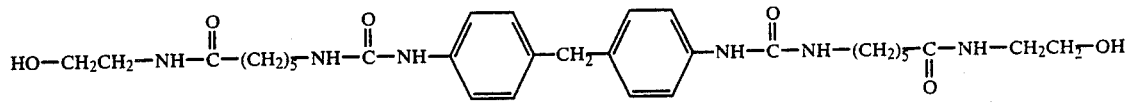

The adduct from Example 5 was reacted with an excess of ethylene glycol as described in Example 2 and the product was isolated in the same manner.

Mp. 154° C.

N Calculated for $C_{31}H_{44}N_4O_8$ (600): 9.3%. Found: 9.1/9.2%.

Example 7

Hexane-1,6-bis-ureido caproic acid-2-hydroxyethylamide (according to the invention)

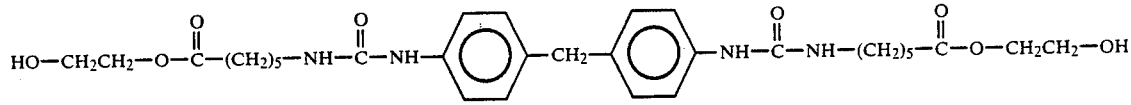

20 g of sodium methylate solution (30% in methanol) were added to 1000 ml of anhydrous toluene and the methanol was distilled off together with a small amount of toluene. 394 g (1 mol) of the lactam adduct from Example 1 were then stirred in and 122 g (2 mol) of ethanolamine were added dropwise at 100° C. in the course of 10 minutes. Stirring was then continued for one hour at 100° C. and the precipitate formed was suction filtered, washed with ethanol and dried. The yield is more than 80% of the theoretical yield even without the mother liquor being worked up. The product is recrystallized from ethanol/water 1:1.

Mp. 204°–205° C.

N Calculated for $C_{24}H_{48}N_6O_6$ (516): 16.3%. Found: 16.4/16.3%.

IR spectrum: 1645 cm$^{-1}$, 1618 cm$^{-1}$ (urea, amide), 1580 cm$^{-1}$, 1550 cm$^{-1}$ (NH deformation oscillation).

Example 8

4,4'-diphenylmethane-bis-ureido caproic acid-2-hydroxyethyl-amide

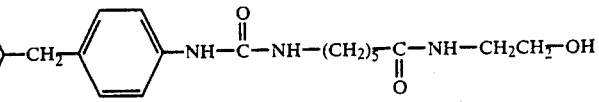

15 g of sodium methylate solution were added to 3000 g (49.2 mol) of ethanolamine and the methanol was distilled off under vacuum at 70° C. 1500 g (3.15 mol) of the lactam adduct from Example 5 were then stirred in, whereupon a bulky precipitate began to separate after 15 minutes. The reaction mixture was diluted with a further 3000 g of ethanolamine to facilitate stirring and the temperature was raised to 100° C. After a further reaction time of 4 hours, the product was suction filtered and washed with ethanol.

Mp. 217° C.

N Calculated for $C_{31}H_{46}N_6O_6$ (598): 14.05%. Found: 13.8/14.0%.

IR spectrum: 1635 cm$^{-1}$ with shoulder at 1650 cm$^{-1}$ (amide, urea), 1600 cm$^{-1}$ (aromatic) 1560, 1510 cm$^{-1}$ (NH deformation oscillations).

Examples 9 to 14

(use according to the invention for the preparation of polyurethanes)

Example 9

100 g of an isocyanate prepolymer based on a linear polypropylene glycol ether diol (molecular weight 2000, OH number 56) and 4,4'-diisocyanatodiphenylmethane (molar ratio of polyol to diisocyanate as 1:2) having an isocyanate group content of 3.55% by weight were homogeneously stirred together with 42.8 g of a high melting diol from Example 2 (particle size in the region of 20 to 100 μm). This reaction mixture had a storage time of several days at room temperature (no change in viscosity). It was only after the addition of 0.1 g of dibutyl tin dilaurate that a slow increase in viscosity occurred at room temperature. Solidification of the reaction mixture could be completed within a short time by heating. Semi-rigid cellular elastomers having a density of 0.5 g/cm³ were thus obtained after one hour at 120°–130° C.

Example 10

124 g of the diol from Example 3 were added to 200 g of a linear polyester of adipic acid, 1,6-hexanediol and neopentyl glycol (molar ratio of diols 65:35, molar weight 2000, OH number 56) at 60°–70° C. and stirred to form a homogeneous mixture. The mixture was degasified in a vacuum with stirring. 70.1 g of 4,4'-diisocyanatodiphenylmethane in the form of a melt (40°–45° C.) and 0.2 g of lead-II-2-ethyl-hexanoate dissolved in gasoline used for cleaning purposes (Octa-Soligen-Pb-24 of Borschers, D-4000, Düesseldorf) were then slowly added. After about 5 minutes stirring under vacuum, the reaction mixture was introduced into a plate mold measuring 20×20×0.5 (internal dimensions in cm) treated with a mold release agent on silicone oil basis ("Trennmittel V, sold by Bayer AG, D-5090 Leverkusen), After 3 hours heating at 120° C., a polyurethane elastomer having the following properties was removed:

| Hardness (Shore A) | 83 |
| Tensile strength (MPa) | 13.4 |
| Elongation at break (%) | 250 |
| Elasticity (%) | 25. |

Example 11

5 g of diisocyanatodiphenylmethane and 31.1 g of the diol from Example 2 were added to 100 g of an isocyanate prepolymer based on a polyester of adipic acid, 1,6-hexanediol and neopentyl glycol (as in Example 10) and 2,4-diisocyanatotoluene (molar ratio of diisocyanate to polyol as 2:1, isocyanate group content 3.4% by weight). The reaction mixture was homogenized at 50° to 60° C. and degasified under vacuum. 0.2 g of lead-II-2-ethylhexanoate were then added. The resulting suspension was heated to 130° C. for 3 hours in a plate mold as described in Example 10. An elastic plate having a hardness of 75 to 80 (Shore A) was obtained.

Example 12

5 g of 4,4'-diisocyanatodiphenylmethane and 34.5 g of the diol from Example 3 were added in a finely divided form to 100 g of the isocyanate prepolymer described in Example 11 and stirred in until homogeneously mixed. The viscosity of the mixture did not change over several days at room temperature. The suspension was degasified under vacuum at 50° to 60° C. with stirring. 0.2 g of lead-II-2-ethylhexanoate was added and the mixture was heated in a mold at 130° C. for 3 hours. A highly elastic molded product having a Shore A hardness of 75 was obtained.

Example 13

The mixture of the isocyanate prepolymer (100 g) described in Example 9 and 5 g of 4,4'-diisocyanatodiphenylmethane was homogeneously mixed with 38.7 g of the diol from Example 2 with stirring at room temperature and the resulting suspension was degasified under vacuum at 50° to 60° C. with stirring. No reaction took place at this temperature, i.e. no change in viscosity was observed at this temperature over a period of several hours. It was only after the addition of 0.2 g of lead-II-2-ethylhexanoate that polyaddition slowly set in. Curing was completed within 3 hours at a temperature of 130° C. in a plate mold. A plate of a polyurethane elastomer having the following mechanical properties was obtained:

| Hardness (Shore A) | 73 |
| Tensile strength (MPa) | 7.8 |
| Elongation at break (%) | 150 |
| Elasticity (%) | 32. |

Example 14

1400 g (0.292 mol) of a polyether triol having a molecular weight of 4800 and an OH number of 35 and containing predominantly primary hydroxyl groups, prepared by the addition of propylene oxide followed by ethylene oxide to trimethylolpropane as starter, were reacted with 435.9 g (1.744 mmol) of 4,4'-diisocyanatodiphenylmethane to form a polyurethane prepolymer containing isocyanate groups. 95.7 parts by weight of this prepolymer were mixed with 54.34 parts by weight of an adduct of 4,4'-diisocyanatodiphenylmethane and tripropylene glycol (isocyanate group content 23% by weight). This mixture had an isocyanate group content of 12.0% by weight. It was mixed with 102.5 parts by weight of the product from Example 5 and homogenized to form a fluid paste. The particle size of the solid diol was less than 100 μm. After the addition of 0.15 parts by weight of lead octoate, the product was completely degasified in a vacuum with stirring. No change in viscosity was found after more than a month's storage at room temperature. Test pieces 2 cm in width of untreated SMC polyester resin and of sheet iron (Fe) degreased with methylene chloride were arranged to overlap by 1 cm and glued together, and the bonds were cured by heating to 140° C. (15 minutes). The following shear strengths were measured:

| SMC/SMC | 2.6–3.8 N/mm². |
| Fe/Fe | 2.3–4.0 N/mm². |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Polyhydroxy compounds containing urea groups and either ester or amide groups and corresponding to the general formulae (I) or (II)

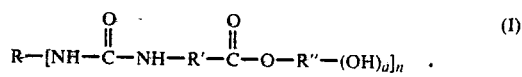

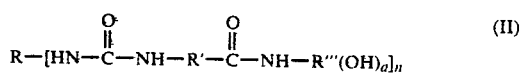

wherein

R represents the residue of an aliphatic, cycloaliphatic, aromatic or heterocyclic polyisocyanate which may be modified, or of an isocyanate prepolymer, said residue having the valency n;

R' represents a $C_3$ to $C_{11}$-alkylene residue;

R'' represents a residue of a polyhydric alcohol having the functionality (a+1);

R'" represents the residue of a monoamino alcohol having a hydroxyl functionality (a);

a is an integer having a value ≧1; and n represents a value from 2 to 6.

2. The composition of claim 1 wherein R represents a $C_2$–$C_{36}$-alkylene, a $C_5$–$C_{15}$-cycloalkylene, or a $C_6$–$C_{15}$-arylene radical.

3. The compound of claim 1 wherein R' represents a $C_3$, $C_4$, $C_5$, $C_{10}$ or $C_{11}$ alkylene radical.

4. The compound of claim 3 wherein R' represents a $C_5$-alkylene radical.

5. The compound of claim 1 wherein a is an integer of from 1 to 5.

6. The compound of claim 5 wherein a is an integer of from 1 to 3.

7. The compound of claim 6 wherein a is 1 or 2.

8. The compound of claim 1 wherein n represents a value of from 2 to 3.

9. Polyhydroxy compounds corresponding to formulae (I) and (II), according to claim 1, wherein R represents a residue corresponding to one of the following formulae

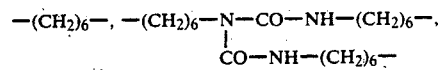

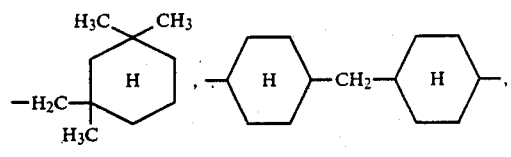

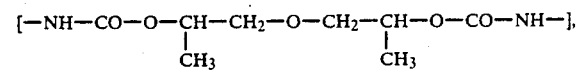

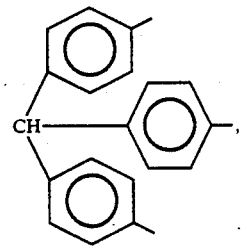

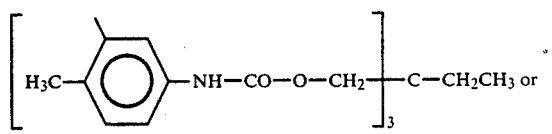

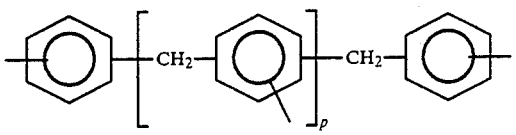

wherein p=0–5,

R' represents a residue corresponding to one of the following formulae —$(CH_2)_3$—, —$(CH_2)_4$—, —$(CH_2)_5$— or —$(CH_2)_{11}$—, R" represents a linear or branched aliphatic group or a cycloaliphatic residue of a polyhydric alcohol having the functionality (a+1) and R'" represents a linear or branched aliphatic or a cycloaliphatic residue of a monoamino alcohol having a hydroxyl functionality (a).

10. A process for the preparation of polyhydroxyl compounds comprising reacting compounds containing carbamoyl lactam groups and corresponding to the general formula (III)

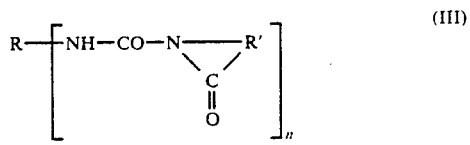

with a polyhydric alcohol of the formula (IV) or a monoamino alcohol of the formula (V)

(IV)     (V)

wherein

R represents the residue of an aliphatic, cycloaliphatic, aromatic or heterocyclic polyisocyanate which may be modified, or of an isocyanate prepolymer, said residue having the valency n;

R' represents a $C_3$ to $C_{11}$-alkylene residue;

R" represents a residue of a polyhydric alcohol having the functionality (a+1);

R'" represents the residue of a monoamino alcohol having a hydroxyl functionality (a);

a is an integer having a value ≧1; and n represents a value from 2 to 6 in the presence of catalytic quantities of strong, basic catalysts from the series of alkali metal base or alkali metal alcoholates, at elevated temperatures of up to 200° C.

11. The process of claim 10, characterized in that the catalyst used is an alkali metal alcoholate derived from the polyhydric alcohol (IV) or amino alcohol (V) used.

12. The process of claim 10, characterized in that the starting materials (III) is an adduct of a lactam and an aliphatic, cycloaliphatic, aromatic or heterocyclic polyisocyanate, or their modification products of prepolymers containing isocyanate groups.

* * * * *